United States Patent [19]

Fest et al.

[11] Patent Number: 4,766,136
[45] Date of Patent: Aug. 23, 1988

[54] PHENYLSULPHONYL-PYRIDINE ALDOXIMES AS FUNGICIDES

[75] Inventors: Christa Fest, Wuppertal; Wilhelm Brandes, Leichlingen; Gerd Hänssler; Paul Reinecke, both of Leverkusen, all of Fed. Rep. of Germany

[73] Assignee: Bayer Aktiengesellschaft, Leverkusen, Fed. Rep. of Germany

[21] Appl. No.: 22,318

[22] Filed: Mar. 3, 1987

[30] Foreign Application Priority Data

Mar. 13, 1986 [DE] Fed. Rep. of Germany ....... 3608382

[51] Int. Cl.⁴ .................... A01N 43/40; C07D 213/78
[52] U.S. Cl. ...................................... 514/357; 546/331
[58] Field of Search ......................... 546/331; 514/357

[56] References Cited

U.S. PATENT DOCUMENTS 3,258,464 6/1966 Sasse et al. ........................... 546/331
4,501,746 2/1985 Krumkelns .......................... 546/331

FOREIGN PATENT DOCUMENTS 423350 4/1967 Switzerland .
643563 6/1984 Switzerland .

OTHER PUBLICATIONS

Lee, S. L. et al, J. Pharm. Sci., vol. 56, No. 10, pp. 1354–1357 (1967).

*Primary Examiner*—Mary C. Lee
*Assistant Examiner*—Dale A. Bjorkman
*Attorney, Agent, or Firm*—Sprung Horn Kramer & Woods

[57] ABSTRACT

Novel fungicidally active phenylsulphonyl-pyridine aldoximes of the formula

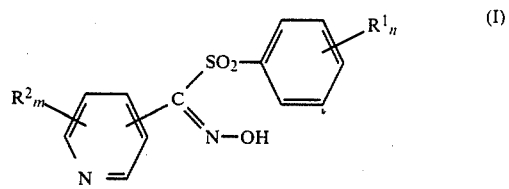

in which
$R^1$ represents halogen, alkyl, alkoxy, alkylthio, halogenoalkyl, halogenoalkoxy, halogenoalkylthio, nitro, alkoxycarbonyl or alkylcarbonylamino,
$R^2$ represents halogen or alkyl,
n represents an integer 0, 1, 2, 3, 4 or 5, and
m represents an integer 0, 1, 2, 3 or 4.

13 Claims, No Drawings

PHENYLSULPHONYL-PYRIDINE ALDOXIMES AS FUNGICIDES

The present invention relates to new phenylsulphonyl-pyridine aldoximes, a process for their preparation, and their use as pesticides, particularly as fungicides, and as intermediates for further highly active compounds.

A series of aldoxime derivatives are already known. Thus, for example, arylsulphonylbenzaldoximes, such as α-phenylsulphonyl-2,6-dichlorobenzaldoxime, and their use as pesticides, above all their use in agents for combating bunt, are known (cf. Swiss Pat. No. 423,350).

New phenylsulphonyl-pyridine aldoximes of the general formula (I)

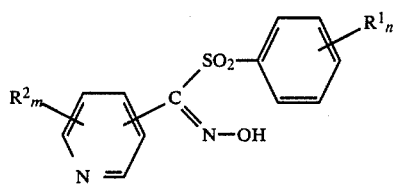

have been found in which
  $R^1$ represents halogen, alkyl, alkoxy, alkylthio, halogenoalkyl, halogenoalkoxy, halogenoalkylthio, nitro, alkoxycarbonyl or alkylcarbonylamino,
  $R^2$ represents halogen or alkyl,
  n represents an integer 0, 1, 2, 3, 4 or 5, and
  m represents an integer 0, 1, 2, 3 or 4,
where the substituents in the rings may be identical or different.

It has furthermore been found that the phenylsulphonyl-pyridine aldoximes of the general formula (I)

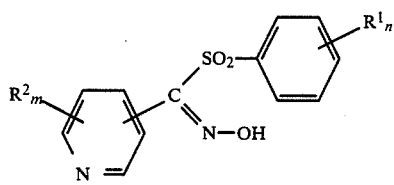

in which
  $R^1$ represents halogen, alkyl, alkoxy, alkylthio, halogenoalkyl, halogenoalkoxy, halogenoalkylthio, nitro, alkoxycarbonyl or alkylcarbonylamino,
  $R^2$ represents halogen or alkyl,
  n represents an integer 0, 1, 2, 3, 4 or 5, and
  m represents an integer 0, 1, 2, 3 or 4,
where the substituents in the rings may be identical or different, are obtained when pyridine aldoximes of the general formula (II)

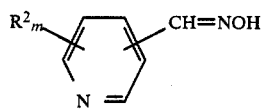

are reacted with chlorine in a solvent to form α-chloropyridine aldoximes of the formula (IIa)

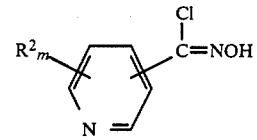

in which
  $R^2$ and m have the above-mentioned meanings,
and these are subsequently reacted with sulphinic acids of the general formula (III)

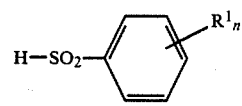

or their alkali metal salts, in which
  $R^1$ and n have the above-mentioned meanings,
if appropriate in the presence of a solvent or diluent and if appropriate in the presence of an acid acceptor.

The phenylsulphonylpyridine aldoximes of the formula (I) according to the invention have strong biological, above all fungicidal, properties.

Surprisingly, the compounds according to the invention display here a considerably stronger, above all fungicidal action than those compounds known from the prior art which are very similar compounds structurally and/or regarding their action.

The compounds of the formula (I) according to the invention can be produced as syn or anti isomers, or as their mixtures in various compositions. The invention relates both to the pure isomers and to the isomeric mixtures.

The alkyl radicals $R^1$ and $R^2$ and the alkyl parts in the alkoxy radicals in $R^1$ may be straight-chain or branched and preferably contain 1 to 6, particularly 1 to 4, carbon atoms in each case. Examples which may be mentioned are: methyl, ethyl, n-propyl, iso-propyl, n-butyl, sec.-butyl, iso-butyl, tert.-butyl, n-pentyl, isopentyl, sec.-pentyl, n-hexyl, sec.-hexyl, methoxy, ethoxy, n-propoxy, iso-propoxy, n-butoxy, iso-butoxy, sec.-butoxy, tert.-butoxy, n-pentoxy, iso-pentoxy, sec.-pentoxy, n-hexoxy and sec.-hexoxy.

The alkylthio radicals in $R^1$ may be straight-chain or branched and preferably contain 1 to 6, particularly 1 to 4, particularly preferably 1 to 3, carbon atoms. Examples which may be mentioned are: methylthio, ethylthio, n-propylthio, iso-propylthio, n-butylthio, iso-butylthio, sec.-butylthio, tert.-butylthio, n-pentylthio and n-hexylthio.

The halogenoalkyl parts in $R^1$ in the halogenoalkyl, halogenoalkoxy and halogenoalkylthio radicals preferably contain 1 to 6, particularly 1 to 4, particularly preferably 1 or 2, carbon atoms and preferably 1 to 9, particularly 1 to 5, particularly preferably 1 to 4, identical or different halogen atoms in each case. Examples which may be mentioned are: trichloromethyl, trifluoromethyl, dichlorofluoromethyl, trichloroethyl, tetrachloroethyl, trichloromethoxy, trichloroethoxy, tetrachloroethoxy, trichloromethylthio, trifluoromethylthio, dichlorofluoromethylthio, trichloroethylthio and tetrachloroethylthio.

In $R^1$ and $R^2$, and in the radicals such as halogenoalkyl, halogen denotes fluorine, chlorine, bromine or iodine, particularly fluorine or chlorine, if not otherwise defined elsewhere.

Alkoxycarbonyl and alkylcarbonylamino in $R^1$ preferably contain 1 to 4, particularly 1 to 3, carbon atoms, particularly preferably 1 to 2 carbon atoms, in the alkyl parts in each case. Examples which may be mentioned are: methoxycarbonyl, ethoxycarbonyl, n-propoxycarbonyl, iso-propoxycarbonyl, n-butoxycarbonyl, sec.-butoxycarbonyl, iso-butoxycarbonyl, tert.-butoxycarbonyl, methylcarbonylamino, ethylcarbonylamino, n-propylcarbonylamino, iso-propylcarbonylamino, n-butylcarbonylamino, isobutylcarbonylamino, sec.-butylcarbonylamino and tert.-butylcarbonylamino.

n preferably denotes 0, 1, 2, 3 or 4, particularly 0, 1, 2 or 3.

m preferably denotes 0, 1, 2 or 3, particularly 0 or 1.
The phenylsulphonyl-pyridine aldoximes according to the invention are generally defined by the formula (I). Preferred compounds of the formula (I) are those in which $R^1$ represents halogen, alkyl or alkoxy having 1 to 6 carbon atoms in each case, alkylthio having 1 to 6 carbon atoms, halogenoalkyl, halogenoalkoxy or halogenoalkylthio having 1 to 6 carbon atoms in each case and 1 to 9 identical or different halogen atoms in each case, nitro, alkoxycarbonyl or alkylcarbonylamino having 1 to 4 carbon atoms in the alkoxy or alkyl part, $R^2$ represents halogen or alkyl having 1 to 6 carbon atoms, n represents an integer 0, 1, 2, 3 or 4, and m represents an integer 0, 1, 2 or 3.

Particularly preferred compounds of the formula (I) are those in which $R^1$ represents halogen, straight-chain or branched alkyl having 1 to 4 carbon atoms, straight-chain or branched alkoxy having 1 to 4 carbon atoms, straight-chain or branched alkylthio having 1 to 4 carbon atoms, halogenoalkyl having 1 to 4 carbon atoms and 1 to 5 identical or different halogen atoms, halogenoalkoxy or halogenoalkylthio having 1 to 4 carbon atoms in each case and 1 to 5 identical or different halogen atoms in each case, nitro, straight-chain or branched alkoxycarbonyl having 1 to 3 carbon atoms, or alkylcarbonylamino having 1 to 3 carbon atoms in the alkyl part, $R^2$ represents halogen or straight-chain or branched alkyl having 1 to 4 carbon atoms, n represents an integer 0, 1, 2, 3 or 4, and m represents an integer 0, 1, 2 or 3.

Compounds of the formula (I) which may particularly be mentioned are those in which $R^1$ represents fluorine, chlorine, straight-chain or branched alkyl or alkoxy having 1 to 4 carbon atoms in each case, straight-chain or branched alkylthio having 1 to 3 carbon atoms, halogenoalkyl, halogenoalkoxy or halogenoalkylthio having 1 or 2 carbon atoms in each case and 1 to 4 identical or different fluorine and chlorine atoms in each case, nitro, alkoxycarbonyl or alkylcarbonylamino having 1 or 2 carbon atoms in the alkoxy or alkyl part in each case, $R^2$ represents fluorine, chlorine or straight-chain or branched alkyl having 1 to 4 carbon atoms, n represents an integer 0, 1, 2, 3 or 4, and m represents an integer 0, 1, 2 or 3.

Compounds of the formula (I) which may be very particularly preferably mentioned are those in which $R^1$ represents fluorine, chlorine, methyl, ethyl, n-propyl, iso-propyl, methoxy, ethoxy, methylthio, trifluoromethyl, trifluoromethoxy, trifluoromethylthio, nitro, methoxycarbonyl, ethoxycarbonyl, methylcarbonylamino or ethyl-carbonylamino, $R^2$ represents chlorine, methyl or ethyl, n represents an integer 0, 1, 2 or 3, and m represents an integer 0 or 1.

If pyrid-2-ylaldoxime, chlorine and sodium 4-methylphenylsulphinate are used as starting materials, then the course of the reaction of the process according to the invention can be illustrated by the following equation:

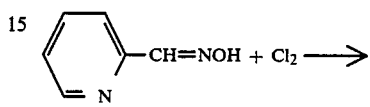

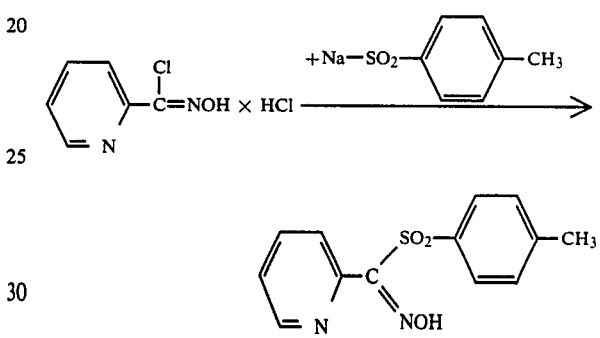

The pyridine aldoximes which are required as starting materials for carrying out the process according to the invention are defined by the formula (II). These substances are known and can be prepared by generally conventional processes (see Houben Weyl, Methods of organic Chemistry, Vol. XII, pages 1095ff).

The phenylsulphinic acids of the formula (III) and their alkali metal salts are also known compounds of organic chemistry (see Beilsteins handbook of organic chemistry, Vol. II, page 2 (4. edition).

The process according to the invention can be carried out, if appropriate, in the presence of a solvent or diluent. As such, all inert organic solvents are, in principle, suitable. Preferably, hydrocarbons, optionally chlorinated, such as, for example, benzene, toluene, xylene, methylene chloride, chloroform, carbon tetrachloride, chlorobenzene and dichlorobenzene, furthermore ethers such as diethyl and dibutyl ether, glycol dimethyl ether and diglycol dimethyl ether, tetrahydrofuran and dioxane, moreover ketones such as acetone, methyl ethyl, methyl isopropyl and methyl isobutyl ketone, in addition esters, such as methyl and ethyl acetate, furthermore nitriles such as, for example, acetonitrile and propionitrile, benzonitrile, glutarodinitrile, additionally amides such as, for example, dimethylformamide, and alcohols such as, for example, methanol, ethanol and isopropanol, are used.

Conventional inorganic or organic acid binders are suitable as acid acceptors for the process according to the invention. The following may be mentioned as such: for example tert.-amines such as triethylamine, pyridine, triethylenediamine, inter alia.

The reaction temperature of the process according to the invention can be varied within a relatively wide temperature range. In general, the chlorination is carried out at temperatures between $-20°$ C. and $30°$ C., preferably between −10° C. and 20° C., whereas the second stage is carried out at between 0° C. and 50° C., preferably between 20° C. and 30° C.

The reaction is normally carried out under atmospheric pressure.

When carrying out the process according to the invention, the compounds of the formula (II) are, in general, initially introduced in a solvent and dry chlorine is passed in at −15° C., the mixture is worked up as usual, and the α-chloropyridinaldoximes of the formula (IIa) are further reacted with the sulphinic acids of the formula (III). In general, the components (IIa) and (III) are employed in equimolar amounts or the sulphinic acids are employed in a slight excess.

The products are worked up by generally conventional methods.

The active compounds according to the invention have a strong biological action and can be employed in practice for combating undesired pests. The active compounds are suitable, inter alia, for use as pesticides, above all as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The compounds are also starting materials for further highly active compounds. Thus, they can be reacted, for example, with chloroformates to form the corresponding O-alkoxycarbonylaldoximes, which are also good fungicides.

USE EXAMPLES

In the following use examples, the compounds listed below are used as comparison substances:

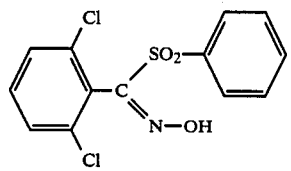

α-phenylsulphonyl-2,6-dichlorobenzaldoxime and

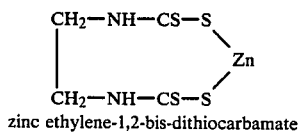

zinc ethylene-1,2-bis-dithiocarbamate

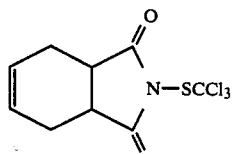

N—trichloromethylthio-tetrahydrophthalimide.

(A)

(B)

(C)

EXAMPLE A

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples at a concentration of 0.025: 7, 9, 8, 4, 6, 5, 1 and 11.

EXAMPLE B

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compound according to preparation Example 1.

EXAMPLE 5

Leptosphaeria nodorum test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to the following preparation examples: 1, 4–9 and 11.

PREPARATION EXAMPLES

Example 1

Precursor:

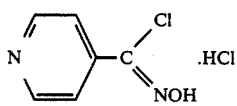

40.6 g (0.333 mol) of pyridin-4-aldoxime are dissolved in 350 ml of methylene chloride, and chlorine (dried) is passed in at −15° C. until saturation has occurred. The reaction mixture is allowed to warm to room temperature overnight, and is then filtered under suction. The reaction product is washed with methylene chloride and then with acetone, and rinsed with ether. 60 g (93.4% of theory) of the desired substance having a melting point of 203° C. (decomposition) are obtained.

Final product:

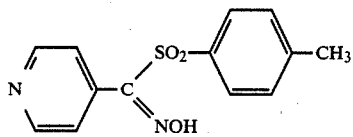

19.3 g (0.1 mol) of α-chloro-pyridine 4-aldoxime hydrochloride are dissolved in 250 ml of methanol, and 18.7 g (0.105 mol) of sodium 4-methylphenylsulphinate are added. 14 ml of triethylamine (0.1 mol) are then added to liberate the α-chloropyridine-4-aldoxime. The reaction proceeds slightly exothermically. The reaction mixture is kept at room temperature, and stirring is continued at this temperature overnight. The mixture is then poured into about 1 l of ice water and stirred, and the reaction product is filtered off under suction, washed, dried and recrystallized from isopropanol. 8.1 g (29% of theory) of the desired compound having a melting point of 138° C. are obtained.

The compounds of the formula (I)

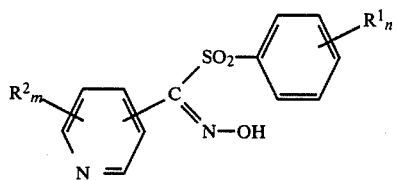

can be prepared analogously to Example 1:

| Example No. | $R^1$ | $R^2$ | n | m | Position of the pyridine ring | Physical data (melting point °C.) |
|---|---|---|---|---|---|---|
| 2 | — | — | 0 | 0 | 4 | 151 |
| 3 | 4-Cl | — | 1 | 0 | 4 | 125 |
| 4 | 4-CH$_3$ | — | 1 | 0 | 3 | 140 (decomp.) |
| 5 | — | — | 0 | 0 | 3 | 126 (decomp.) |
| 6 | 4-Cl | — | 1 | 0 | 3 | 139 (decomp.) |
| 7 | 4-CH$_3$ | — | 1 | 0 | 2 | 133 (decomp.) |
| 8 | — | — | 0 | 0 | 2 | 113 (decomp.) |
| 9 | 4-Cl | — | 1 | 0 | 2 | 131 |
| 10 | 4-CH$_3$ | 6-CH$_3$ | 1 | 1 | 2 | 142 |
| 11 | — | 6-CH$_3$ | — | 1 | 2 | 128 |
| 12 | 4-OCH$_3$ | — | 1 | 0 | 2 | 142 (decomp.) |
| 13 | 3-CF$_3$ | — | 1 | 0 | 2 | 120 (decomp.) |
| 14 | 4-F | — | 1 | 0 | 2 | 123 (decomp.) |

It is understood that the specification and examples are illustrative but not limitative of the present invention and that other embodiments within the spirit and scope of the invention will suggest themselves to those skilled in the art.

Example 1 can be reacted, for example, with chloroformates to form the corresponding O-alkoxycarbonylaldoxime (IA) which is also a good fungicide.

EXAMPLE A

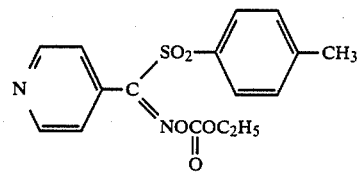

13,8 g (0.05 mol) α-(4-methylphenylsulfonyl)-pyridine-4-aldoxime are dissolved in 150 ml acetonitril and 7 ml (0.05 mol) triethylamine and 5.5 g (0.05 mol) chloroformic acid ether ester are added.

The reaction proceeds exothermically. The reaction mixture is kept at room temperature, and stirring is continued at this temperature overnight.

The mixture is then poured into 750 ml water and stirred, and the reaction product is filtered off, washed and dried and recrystallized from isopropanol. 7.4 g (43% of theory) of the desired compound having a melting point of 126° C. are obtained.

We claim:

1. A phenylsulphonyl-pyridine aldoxime of the formula

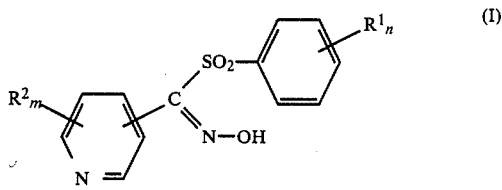

in which
$R^1$ represents halogen, alkyl, alkoxy, alkylthio, halogenoalkyl, halogenoalkoxy, halogenoalkylthio, nitro, alkoxycarbonyl or alkylcarbonylamino,
$R^2$ represents halogen or alkyl,
n represents an integer 0, 1, 2, 3, 4 or 5, and
m represents an integer 0, 1, 2, 3 or 4.

2. A phenylsulphonyl-pyridine aldoxime according to claim 1, in which
$R^1$ represents halogen, alkyl or alkoxy having 1 to 6 carbon atoms in each case, alkylthio having 1 to 6 carbon atoms, halogenoalkyl, halogenoalkoxy or halogenoalkylthio having 1 to 6 carbon atoms in each case and 1 to 9 identical or different halogen atoms in each case, nitro, alkoxycarbonyl or alkylcarbonylamino having 1 to 4 carbon atoms in the alkoxy or alkyl part,
$R^2$ represents halogen or alkyl having 1 to 6 carbon atoms,
n represents an integer 0, 1, 2, 3 or 4, and
m represents an integer 0, 1, 2 or 3.

3. A phenylsulphonyl-pyridine aldoxime according to claim 1, in which
$R^1$ represents halogen, straight-chain or branched alkyl having 1 to 4 carbon atoms, straight-chain or branched alkoxy having 1 to 4 carbon atoms, straight-chain or branched alkylthio having 1 to 4 carbon atoms, halogenoalkyl having 1 to 4 carbon atoms and 1 to 5 identical or different halogen atoms, halogenoalkoxy or halogenoalkylthio having 1 to 4 carbon atoms in each case and 1 to 5 identical or different halogen atoms in each case, nitro, straight-chain or branched alkoxycarbonyl having 1 to 3 carbon atoms, or alkylcarbonylamino having 1 to 3 carbon atoms in the alkyl part, $R^2$ represents halogen or straight-chain or branched alkyl having 1 to 4 carbon atoms, n represents an integer 0, 1, 2, 3 or 4, and m represents an integer 0, 1, 2 or 3.

4. A phenylsulphonyl-pyridine aldoxime according to claim 1, in which $R^1$ represents fluorine, chlorine, straight-chain or branched alkyl or alkoxy having 1 to 4 carbon atoms in each case, straight-chain or branched alkylthio having 1 to 3 carbon atoms, halogenoalkyl, halogenoalkoxy or halogenoalkylthio having 1 or 2 carbon atoms in each case and 1 to 4 identical or different fluorine and chlorine atoms in each case, nitro, alkoxycarbonyl or alkylcarbonylamino having 1 or 2 carbon atoms in the alkoxy or alkyl part in each case, $R^2$ represents fluorine, chlorine or straight-chain or branched alkyl having 1 to 4 carbon atoms, n represents an integer 0, 1, 2, 3 or 4, and m represents an integer 0, 1, 2 or 3.

5. A phenylsulphonyl-pyridine aldoxime according to claim 1, in which $R^1$ represents fluorine, chlorine, methyl, ethyl, n-propyl, iso-propyl, methoxy, ethoxy, methylthio, trifluoromethyl, trifluoromethoxy, trifluoromethylthio, nitro, methoxycarbonyl, ethoxycarbonyl, methylcarbonylamino or ethylcarbonylamino, $R^2$ represents chlorine, methyl or ethyl, n represents an integer 0, 1, 2 or 3, and m represents an integer 0 or 1.

6. A compound according to claim 1 wherein such compound is oximino-pyrid-3-yl-p-tolylsulphonyl-methane of the formula

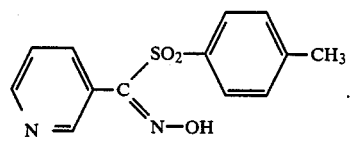

7. A compound according to claim 1 wherein such compound is oximino-pyrid-3-yl-p-chlorophenylsulphonyl-methane of the formula

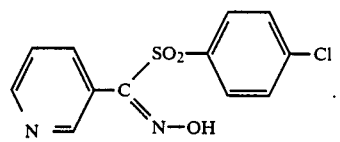

8. A compound according to claim 1 wherein such compound is oximino-(6-methyl-pyrid-2-yl)-phenylsulphonyl-methane of the formula

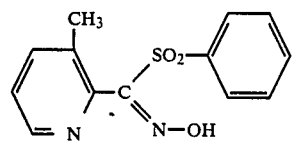

9. A compound according to claim 1 wherein such compound is oximino-pyrid-2-yl-p-tolylsulphonyl-methane of the formula

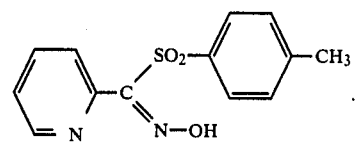

10. A compound according to claim 1 wherein such compound is oximino-pyrid-2-yl-p-chlorophenylsulphonyl-methane of the formula

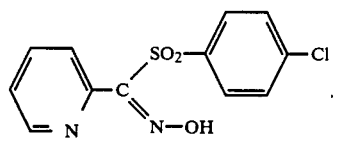

11. A fungicidal composition comprising a fungicidally effective amount of a phenylsulphonyl-pyridine aldoxime according to claim 1 and a diluent.

12. A method of combating fungi which comprises applying to such fungi or to a fungus habitat a fungicidally effective amount of a phenylsulphonyl-pyridine aldoxime according to claim 1.

13. The method according to claim 12, wherein such phenylsulphonyl-pyridine aldoxime is
oximino-pyrid-3-yl-p-tolylsulphonyl-methane,
oximino-pyrid-3-yl-p-chlorophenylsulphonyl-methane,
oximino-(6-methyl-pyrid-2-yl)-phenylsulphonyl-methane,
oximino-pyrid-2-yl-p-tolylsulphonyl-methane or
oximino-pyrid-2-yl-p-chlorophenylsulphonyl-methane.

* * * * *